(12) United States Patent
Castellana

(10) Patent No.: US 12,156,927 B2
(45) Date of Patent: Dec. 3, 2024

(54) FORMULATION FOR ODONTOLOGICAL AND DERMATOLOGICAL USE CONTAINING TRCHLOROACETATE SALTS AND HYDROXYACIDS

(71) Applicant: Rossana Castellana, Trieste (IT)

(72) Inventor: Rossana Castellana, Trieste (IT)

(73) Assignee: GPQ S.R.L., Milan (IT)

( * ) Notice: Subject to any disclaimer, the term of this patent is extended or adjusted under 35 U.S.C. 154(b) by 475 days.

(21) Appl. No.: 17/596,426

(22) PCT Filed: Jun. 22, 2020

(86) PCT No.: PCT/EP2020/067350
§ 371 (c)(1),
(2) Date: Dec. 10, 2021

(87) PCT Pub. No.: WO2020/260199
PCT Pub. Date: Dec. 30, 2020

(65) Prior Publication Data
US 2022/0304904 A1    Sep. 29, 2022

Related U.S. Application Data

(60) Provisional application No. 62/865,364, filed on Jun. 24, 2019.

(51) Int. Cl.
| | | |
|---|---|---|
| *A61K 8/19* | (2006.01) | |
| *A61K 8/36* | (2006.01) | |
| *A61K 8/73* | (2006.01) | |
| *A61Q 19/08* | (2006.01) | |

(52) U.S. Cl.
CPC ............ *A61K 8/19* (2013.01); *A61K 8/36* (2013.01); *A61K 8/731* (2013.01); *A61Q 19/08* (2013.01)

(58) Field of Classification Search
CPC . A61K 8/19; A61K 8/36; A61K 8/731; A61Q 19/08
See application file for complete search history.

(56) References Cited

U.S. PATENT DOCUMENTS

| | | |
|---|---|---|
| 6,333,356 B1 | 12/2001 | Ptchelintsev et al. |
| 2004/0208906 A1 | 10/2004 | Tatara et al. |
| 2014/0042027 A1* | 2/2014 | Belisle ............ G01N 27/44726 204/461 |
| 2017/0296613 A1* | 10/2017 | Hendriks ............ A61K 31/375 |

FOREIGN PATENT DOCUMENTS

| | | | |
|---|---|---|---|
| EP | 2241303 A2 | 10/2010 | |
| EP | 3006016 A1 | 4/2016 | |
| JP | 6225228 B2 * | 11/2017 | ........... A61K 31/198 |
| RU | 2558061 C2 | 7/2015 | |
| WO | 2010105052 A1 | 9/2010 | |
| WO | 2019058249 A1 | 3/2019 | |

OTHER PUBLICATIONS

Nabil Fanous et al., "Universal Trichloroacetic Acid Peel Technique for Light and Dark Skin," in JAMA Facial Plastic Surgery, 2017 (Year: 2017).*
Charitomeni V. et al., "Chemical peeling with trichloroacetic acid and lactic acid for infraorbital dark circles", Journal of Cosmetic Dermatology, vol. 12, No. 3, 1 September 20213., pp. 204-209.
International Preliminary Report on Patentability of PCT/EP2020/067350 of Oct. 5, 2021.
Roth, P.T., "40% triple acid peel", GNPD Mintel, Feb. 1, 2014, abstract.
Search Report and Written Opinion of PCT/EP2020/067350 of Sep. 23, 2020.
Communication from foreign associated reporting office action issued Nov. 17, 2023 in connection with counterpart Russian Patent Application 2022101371.
English Translation of the Office Action issued in counterpart Russian Application No. 2022101371 on Nov. 17, 2023.

* cited by examiner

*Primary Examiner* — Blessing M Fubara
(74) *Attorney, Agent, or Firm* — Silvia Salvadori, P.C.; Silvia Salvadori

(57) ABSTRACT

Pharmaceutical, odontological, cosmetic and dermatological compositions comprising addition salts of trichloroacetic acid, one or more hydroxyacids and optionally glutamic acid or glutamic acid bioisosteres and phytic acid are useful for the peeling of the gingival collar, skin peeling, for resurfacing, treating skin hyper pigmentation, control sebum production, acne, pore size reduction and reducing the appearance of scars without causing undesirable side effects and contrast in coloration of the treated skin, for stimulation of the fibroblasts, transdermal biorevitalization, stimulation of the production of new collagen, for aesthetic improvement, for skin lightening, skin beautifying, skin firming and skin rejuvenation.

12 Claims, No Drawings

FORMULATION FOR ODONTOLOGICAL AND DERMATOLOGICAL USE CONTAINING TRCHLOROACETATE SALTS AND HYDROXYACIDS

This application is a U.S. national stage of PCT/EP2020/067350 filed on 22 Jun. 2020, which claims priority to and the benefit of U.S. Provisional Application No. 62/865,364 filed on 24 Jun. 2019, the contents of which are incorporated herein by reference in their entireties.

FIELD OF THE INVENTION

The present invention relates to compositions for pharmaceutical, odontological, cosmetic and dermatological use, particularly for the peeling of the gingival collar, skin peeling, and useful for resurfacing, treating skin hyper pigmentation, control sebum production, for treating acne, for pore size reduction and reducing the appearance of scars without causing undesirable side effects like frosting, scarring, infection, reactivation of herpes simplex infections and contrast in coloration of the treated skin, for stimulation of the fibroblasts, transdermal biorevitalization, stimulation of the production of new collagen, for aesthetic improvement, for skin lightening, skin beautifying, skin firming and skin rejuvenation. These new formulations which contain addition salts of trichloroacetic acid showed antiseptic properties and, inducing the desquamation of the stratum corneum, stimulate the skin cells to form new collagen.

BACKGROUND

It is known that through desquamation the stratum corneum of the skin renew itself and that mature skin may take more time to be renewed if compared to young skin. Firmness and elasticity in the skin depends on the different forces of elastin and collagen: elastin is responsible for the flexibility of the skin whereas collagen's main task is to keep the skin in shape. In young skin with fresh collagen, the skin after a mechanical solicitation returns faster to its original position respect to more aged skin.

The cellular turnover of the epidermal tissues can be increased by treatments that accelerate the rate at which new cells of epidermal tissues are formed. Skin peeling, also known as chemoexfoliation, for the treatment of aged or damaged skin has been used by dermatologists to restore the skin's freshness and youthful appearance and to reduce the appearance of scars.

The outer layers of human skin can be caused to peel by applying chemical formulations able to remove dead skin and to wound underlying living skin tissue.

This treatment is known as "chemical peel" and can be carried out using different chemical agents, for example alpha- and beta-hydroxy acids, trichloroacetic acid, phenols, etc., at appropriate concentration and for a well-defined period of time, either in a single treatment session, or, at most, over a period of repetitive treatments over several days.

Chemical peeling can be done in varying degrees of depth defined as superficial, medium, and deep peels.

Since a superficial peeling penetrates only the epidermis, it produces limited or no undesirable side effects. Commonly used superficial peels are performed using glycolic acid. When properly used, superficial exfoliation with glycolic acid at concentrations of 30 to 50% has demonstrated good clinical efficacy in the treatment of superficial hyperpigmentation, mild-to-moderate chrono—and photoaging and fine rhytides.

The medium and deep peeling damages the entire epidermis, the papillary dermis and create a wound to the level of the midreticular dermis and usually produces redness lasting several days.

Commonly used medium-depth chemoexfoliation is a 50% trichloroacetic acid (TCA) solution which is a frequently used peeling treatment for fine rhytides, actinic photodamage, hyperpigmentation, and even actinic-related premalignant changes, such as actinic keratoses. Other common chemical agents currently used for medium-depth peeling are 70% glycolic acid and 35 to 50% TCA, with or without adjuvant combination products (e.g., Jessner's solution; Monheit, G. D. The Jessner's+TCA Peel: A Medium-Depth Chemical Peel. *J. Dermatol. Surg. Oncol.* 1989, 15(9), 945-950), and multiple layer applications of 20 to 40% salicylic acid and pyruvic acid.

Deep chemical peeling may cause keratocoagulation (i.e., protein denaturation of keratin and collagen) results in a "white frost" to appear on the skin where the chemical agent has been applied or rash or redness of the skin. In this case the post-procedural recovery period might cause limitation to the relational life of the patients.

Different levels of frosting, labelled as levels I, II and III, may be obtained using chemical peeling agents: in level I frosting appears clinically as erythema with a stringy or patchy light frosting, in level II frosting appears as a uniform, white-coated frosting with underlying erythema, in level III frosting appears as solid white enamel frosting with little to no background erythema. With superficial peels, the aim is to have little to no frosting (Soleymani, T.; Lanoue, J.; Rahman, Z. A Practical Approach to Chemical Peels: A Review of Fundamentals and Step-by-step Algorithmic Protocol for Treatment. *J. Clin. Aesthet. Dermatol.* 2018, 11(8): 21-28).

Different types of peeling treatments or protocols have been described with the goal to remove a predictable, uniform thickness of damaged skin, which subsequently allows for normal wound healing and skin rejuvenation to occur, while simultaneously minimizing complications and undesired side effects.

Compounds useful for peeling treatments are hydroxy acids like glycolic acid, citric acid, glucuronic acid, alpha-hydroxybutyric acid, alpha-hydroxy-isobutyric acid, lactic acid, malic acid, mandelic acid, mucic acid, pyruvic acid, galacturonic acid, beta-phenyllactic acid, beta-phenylpyruvic acid, beta-hydroxybutyric acid, glucaric acid, tartaric acid and tartronic acids (U.S. Pat. Nos. 3,988,470, 4,021, 572, 4,197,316, 4,234,599, 4,246,261, 4,380,549 and 4,363, 815).

Compositions for dermatological use comprising trichloroacetic acid (TCA) are generally known (see for example U.S. Pat. Nos. 4,874,361, 5,599,546, 5,716,625, 6,139,850 and 7,189,406). Phytic acid has also been proposed for skin treatment (U.S. Pat. Nos. 5,116,605, 5,434,144, 5,536,499, 5,665,364 and 5,811,111). Formulations comprising phytic acid or trichloroacetic acid as active ingredients are also known (U.S. Pat. No. 7,439,214 and JP 62056411).

The above mentioned compounds and formulations used for chemoexfoliation should be chosen also taking into consideration the skin type of the patient to be treated since it is known that these therapies have to be tailored on the basis of several factors like the genetic disposition (i.e. eye color, hair color/type, the depth of skin capillaries, the thickness of the skin, and the body ability to produce melanin), the tanning habits, according to each subject's specific concerns and wishes for aesthetic improvement of their skin and ability to tolerate the post-procedural recovery period.

New and better topic formulations devoid of the above described side effects (i.e. frosting, etc.) are therefore needed.

The above mentioned formulations developed for chemical peeling, and particularly formulation with TCA, can also be used in odontology as a soft tissue chemical cauterizing agents on gingival margins prior to restoring cervical cavities with resin materials (Khoroushi M., Tavasoli M.; *The effect of trichloroacetic acid as a hemostatic and etching agent on the morphological characteristics and shear bond strength of resin composite to enamel*. Oper Dent. (2010), 35(2), 187-93; Lewinstein I, Rotstein I., (1992). *Effect of trichloroacetic acid on the microhardness and surface morphology of human dentin and enamel*. Endodontics and Dental Traumatology, 1992, 8(1), 16-20). Also, for this intended use TCA is not devoid of side effects which includes reduction of microhardness in both dentin and enamel and possible necrotic effects on marginal gingiva. In order to avoid these side effects, the concentration of TCA and its application is limited to few seconds (ie 30 seconds). Therefore, also for odontological use new and better formulations devoid of the above described side effects are needed.

Definitions

Folliculitis is a skin condition in which hair follicles become inflamed. It is usually caused by a bacterial or fungal infection.

Rhytide is a facial wrinkle secondary to muscular contraction patterns in the skin.

Actinic photodamage is represented by rough patches of skin caused by damage from years of sun exposure.

Hyperpigmentation is the darkening of an area of skin or nails caused by increased melanin.

Keratocoagulation results in a "white frost". It is due to protein denaturation of keratin and collagen.

Hydroxyethylcellulose is a compound identified by the CAS Registry Number 9004-62-0.

Idroramnosan® is a cellulose derivatized with PEG350.

Homocysteic acid is a compound identified by the CAS Registry Number 14857-77-3.

Bioisostere (also named Bioster) is a molecule resulting from the exchange of an atom or of a group of atoms with an alternative, broadly similar, atom or group of atoms (Venkatesan, N.; Ramanathan, M.; Mangayarakarasi, V.; Solairaj, P. Bioisosterism Review—an Biological Modification. *World J. Pharm. Pharm. Sci.* 2017, 6(9), 1918-1949).

Jessner's solution is used as therapeutic agent to treat hyperkeratotic epidermal lesions (Monheit, G. D. The Jessner's+TCA Peel: A Medium-Depth Chemical Peel. *J. Dermatol. Surg. Oncol.* 1989, 15(9), 945-950).

SUMMARY OF THE INVENTION

This invention concerns topical formulations which contain salts of trichloroacetic acid for the treatment of skin defect and skin renewal. Particularly, these formulations reduce the thickness of the epidermis, stimulating the cellular turnover and inducing substantial modification of the dermal compartment with stimulation of the production of fibroblasts and of mature collagen. Said formulations are therefore useful for the elimination of the discolour results of the acne and of the superficial scars.

These new formulations may be in form of liquid solutions, gel formulations or compact gel, depending on the intended use. The positive effects of the use of these new topical formulations on skin firmness and elasticity have been confirmed using instrumental measurements before and after the treatment and by a sensible improvement of the aspect of the skin after clinical treatment.

In comparison with other chemical peeling, the formulations of the invention can reduce the risk of the most common side effects of these treatments like frosting, scarring, infection, reactivation of herpes simplex infections and contrast in coloration of the treated skin.

The formulations of the invention may also be used in odontology for the peeling of the gingival collar. These new formulations are safer than the traditional odontological TCA formulations since devoid of any necrotic effects on marginal gingiva and do not affect the microhardness and structural changes in both dentin and enamel.

DETAILED DESCRIPTION OF THE INVENTION

The aqueous formulations of the invention contain trichloroacetate salts at a concentration ranging between 20 and 40% w/w, preferably 32-34% w/w, one or more hydroxyacids at a concentration ranging between 0.5 and 10% w/w, and optionally glutamic acid or glutamic acid bioisosteres, phytic acid at a concentration ranging between 0.2 and 4.0% w/w, glycerol at a concentration lower than 15% w/w, an oxidant at a concentration lower than 1% w/w, typically from 0.1 to 1%; and a hydrophilic pharmaceutically acceptable gelling agent at a concentration up to 7% w/w, typically from 0.1 to 2%.

The selected trichloroacetate salts include the sodium salt (1:1) (CAS registry number 650-51-1), ammonium salt (1:1) (CAS registry number 7646-88-0), potassium salt (1:1)) (CAS registry number 16586-14-4), magnesium salt (2:1) (CAS registry number 16094-02-3), calcium salt (2:1) (CAS registry number 21348-16-3), zinc salt (2:1) (CAS registry number 16083-12-8) and silver salt (1:1) (CAS registry number 25000-97-9). In a preferred embodiment, the trichloroacetate salts are the ammonium salt (1:1) and the silver salt (1:1), more preferably the ammonium salt (1:1).

The selected hydroxyacids include one or more of the following compounds: tartaric acid, citric acid, glycolic acid, glucuronic acid, alpha-hydroxybutyric acid, alpha-hydroxy-isobutyric acid and lactic acid. In a preferred embodiment, the hydroxyacids are tartaric acid, citric acid and glycolic acid, more preferably tartaric acid and/or citric acid.

The glutamic acid bioisosteres utilized in said formulations include homocysteic acid.

The oxidants include hydrogen peroxide and benzoyl peroxide; hydrogen peroxide is preferably used.

Examples of hydrophilic pharmaceutically acceptable gelling agents include hydroxyethyl cellulose, Idroramnosan®, xanthan gum, sclerotium gum, hydroxypropyl starch phosphate, Sepigel™ 305 and Sepimax™ zen, preferably hydroxyethyl cellulose and Idroramnosan®. The gelling agent may be absent giving origin to liquid and non-viscous formulations or be present in a concentration typically up to 0.8% by weight to afford gel formulations and up to 7% by weight to afford compact gel formulations.

Example 1

25 kg of an aqueous solution with the following composition: tartaric acid (1 Kg), citric acid (4 Kg), demineralized water (20 Kg) were added to an aqueous solution 49.8% w/w of ammonium trichloroacetate (66.3 Kg) under stirring at 20-25° C. A 50% w/w aqueous solution of phytic acid (400 g), 30% hydrogen peroxide (3.3 Kg), demineralized water (4.4 Kg), Idroramnosan® (600 g) were then sequentially added portion wise (in 30') to the obtained solution under stirring at 20-25° C. The obtained mixture was then maintained under stirring at room temperature to obtain a homogeneous solution and then filtered on a suitable 10-micron filter. The pH value of the obtained solution is comprised in the range 1.8÷2.2.

Final Composition of the Formulation

| Components | Quantity | Composition (% weight) |
|---|---|---|
| Demineralized water | 59.9 Kg | 60.2% |
| Tartaric acid | 1.0 Kg | 1.0% |
| Citric acid | 4.0 Kg | 4.0% |
| Ammonium trichloroacetate | 33.0 Kg | 33.0% |
| Phytic acid | 0.2 Kg | 0.2% |
| Hydrogen peroxide | 1.0 Kg | 1.0% |
| Idroramnosan ® | 0.6 Kg | 0.6% |

Example 2

Homocysteic acid (2.0 Kg), a 50% w/w aqueous solution of tartaric acid (2.0 kg), citric acid (4.0 Kg), demineralized water (25.6 Kg) were sequentially added to an aqueous solution 50.2% w/w of ammonium trichloroacetate (65.8 Kg) under stirring at 20-25° C. Hydroxyethylcellulose (600 g) was then added portion wise (in 30') to the obtained solution. The obtained solution was then maintained under stirring at room temperature for 60' and then filtered on a suitable 10-micron filter. The pH value of the obtained solution is comprised in the range 1.8÷2.2.

Final Composition of the Formulation

| Components | Quantity | Composition (% weight) |
|---|---|---|
| Demineralized water | 59.4 Kg | 59.4% |
| Tartaric acid | 1.0 Kg | 1.0% |
| Homocysteic acid | 2.0 Kg | 2.0% |
| Citric acid | 4.0 Kg | 4.0% |
| Ammonium trichloroacetate | 33.0 Kg | 33.0% |
| Hydroxyethylcellulose | 0.6 Kg | 0.6% |

Example 3

Homocysteic acid (2.0 Kg), a 50% w/w aqueous solution of tartaric acid (2.0 kg), citric acid (4.0 Kg), trichloroacetic acid (11.0 Kg), demineralized water (14.6 Kg) were sequentially added to an aqueous solution 50.2% w/w of ammonium trichloroacetate (65.8 Kg) under stirring at 20-25° C. Hydroxyethylcellulose (600 g) was then added portion wise (in 30') to the obtained solution under stirring at room temperature. The obtained solution was then maintained under stirring at room temperature for 60' and then filtered on a suitable 10-micron filter. The pH value of the obtained solution is comprised in the range 0.8÷1.2.

Final Composition of the Formulation

| Components | Quantity | Composition (% weight) |
|---|---|---|
| Demineralized water | 48.4 Kg | 48.4% |
| Tartaric acid | 1.0 Kg | 1.0% |
| Homocysteic acid | 2.0 Kg | 2.0% |
| Citric acid | 4.0 Kg | 4.0% |
| Ammonium trichloroacetate | 33.0 Kg | 33.0% |
| Trichloroacetic acid | 11.0 Kg | 11.0% |
| Hydroxyethylcellulose | 0.6 Kg | 0.6% |

Comparative Example 4

Sodium trichloroacetate (97%; 34.0 Kg) and homocysteic acid (2.5 Kg) were sequentially added under stirring at 20-25° C. to purified water (62.9 Kg). Hydroxyethylcellulose (600 g) was then added portion wise (in 30'). The obtained solution was then maintained under stirring at room temperature for 60' and then filtered on a suitable 10-micron filter. The pH value of the obtained solution is comprised in the range 1.8÷2.2.

Final Composition of the Formulation

| Components | Quantity | Composition (% weight) |
|---|---|---|
| Demineralized water | 62.9 Kg | 62.9% |
| Homocysteic acid | 2.5 Kg | 2.5% |
| Sodium trichloroacetate | 34.0 Kg | 34.0% |
| Hydroxyethylcellulose | 0.6 Kg | 0.6% |

Example 5

Homocysteic acid (2.0 Kg), a 50% w/w aqueous solution of tartaric acid (2.0 kg), citric acid (4.0 Kg), 30% hydrogen peroxide (3.3 Kg), glycerol (10 kg), demineralized water (12.9 Kg) were added sequentially to an aqueous solution 50.2% w/w of ammonium trichloroacetate (65.8 Kg) under stirring at 20-25° C. The obtained solution was then maintained under stirring at room temperature for 60' and then filtered on a suitable 10-micron filter. The pH value of the obtained solution is comprised in the range 1.8÷2.2.

Final Composition of the Formulation

| Components | Quantity | Composition (% weight) |
|---|---|---|
| Demineralized water | 47.9 Kg | 49.0% |
| Tartaric acid | 1.0 Kg | 1.0% |
| Homocysteic acid | 2.0 Kg | 2.0% |
| Citric acid | 4.0 Kg | 4.0% |
| Ammonium trichloroacetate | 33.0 Kg | 33.0% |
| Glycerol | 10.0 Kg | 10.0% |
| Hydrogen peroxide | 1.0 Kg | 1.0% |

Example 6

Homocysteic acid (2.0 Kg), citric acid (0.6 Kg), tartaric acid (0.2 Kg), 50% w/w aqueous solution of phytic acid (400 g), glycerol (10.0 kg) and demineralized water (19.8 Kg) were sequentially added to 49.7% w/w aqueous solution of ammonium trichloroacetate (66.4 Kg), under stirring at 20-25° C. Hydroxyethylcellulose (600 g) was then added portion wise (in 30') To the obtained solution. The obtained solution was then maintained under stirring at room temperature for 60' and then filtered on a suitable 10-micron filter. The pH value of the obtained solution is comprised in the range 1.8÷2.2.

Final Composition of the Formulation

| Components | Quantity | Composition (% weight) |
|---|---|---|
| Ammonium trichloroacetate | 33.0 Kg | 33.0% |
| Homocysteic acid | 2.0 Kg | 2.0% |
| Citric acid | 0.6 Kg | 0.6% |
| Tartaric acid | 0.2 Kg | 0.2% |
| Phytic acid | 0.2 Kg | 0.2% |
| Glycerol | 10.0 Kg | 10.0% |
| Demineralized water | 53.4 Kg | 53.4% |
| Hydroxyethylcellulose | 0.6 Kg | 0.6% |

Example 7

Homocysteic acid (2.0 Kg), citric acid (0.6 Kg), tartaric acid (0.2 Kg), 50% w/w aqueous solution of phytic acid (400 g), glycerol (10.0 kg), 30% hydrogen peroxide (3.3 Kg) and demineralized water (12.1 Kg) were sequentially added to 49.7% w/w aqueous solution of ammonium trichloroacetate (66.4 Kg), under stirring at 20-25° C. Sepigel™ 305 (5.0 Kg) was then added portion wise (in 30') to the obtained solution. The obtained solution was then maintained under stirring at room temperature for 60' and then filtered on a suitable 10-micron filter. The pH value of the obtained solution is comprised in the range 1.8÷2.2.

Final Composition of the Formulation

| Components | Quantity | Composition (% weight) |
|---|---|---|
| Ammonium trichloroacetate | 33.0 Kg | 33.0% |
| Homocysteic acid | 2.0 Kg | 2.0% |
| Citric acid | 0.6 Kg | 0.6% |
| Tartaric acid | 0.2 Kg | 0.2% |
| Phytic acid | 0.2 Kg | 0.2% |
| Glycerol | 10.0 Kg | 10.0% |
| Hydrogen peroxide | 1.0 Kg | 1.0% |
| Demineralized water | 48.0 Kg | 48.0% |
| Sepigel ™ 305 | 5.0 Kg | 5.0% |

Example 8

Homocysteic acid (2.0 Kg), citric acid (0.6 Kg), tartaric acid (0.2 Kg), 50% w/w aqueous solution of phytic acid (400 g), glycerol (10.0 kg) and demineralized water (15.4 Kg) were sequentially added to 49.7% w/w aqueous solution of ammonium trichloroacetate (66.4 Kg), under stirring at 20-25° C. Sepigel™ 305 (5.0 Kg) was then added portion wise (in 30') to the obtained solution. The obtained solution was then maintained under stirring at room temperature for 60' and then filtered on a suitable 10-micron filter. The pH value of the obtained solution is comprised in the range 1.8÷2.2.

Final Composition of the Formulation

| Components | Quantity | Composition (% weight) |
|---|---|---|
| Ammonium trichloroacetate | 33.0 Kg | 33.0% |
| Homocysteic acid | 2.0 Kg | 2.0% |
| Citric acid | 0.6 Kg | 0.6% |
| Tartaric acid | 0.2 Kg | 0.2% |
| Phytic acid | 0.2 Kg | 0.2% |
| Glycerol | 10.0 Kg | 10.0% |
| Demineralized water | 49.0 Kg | 49.0% |
| Sepigel ™ 305 | 5.0 Kg | 5.0% |

Cosmetic Tests

Skin Firmness and Elasticity: in order to evaluate the effect of the tested formulations the reference was the untreated skin area of the same subjects. The subjects were treated in a single treatment session with the examined formulations: the formulation was spread on the skin for three-five times (about 0.2 ml each time). This session is repeated once a week for total three weeks. The examined subjects were women aged between 40 and 80 years. The effect of the formulation, performed treating a 100 cm² area of the skin, was evaluated by visual inspection, by using "VISTA® Skin Analysis system" and "Antera 3D Camera for skin analysis" ANTERA 3D® MIRAVEX Ser. No. 12/371,150 (serial number) Version 2.1.8-it-Pro (http://miravex.com/antera-3d/), of the treated skin against the untreated skin (Table 1) before the treatment and at the end of the treatment.

By the above mentioned analyses, and particularly by the acquisition and quantitative evaluation of the wrinkles (depth, width and overall size; Table 1), of the examined patients before and after the treatment with the formulation 7 we observed a sensible improvement of the aspect of the treated skin surface with a decrease of the average depth, average width and overall size of the wrinkles respectively of −34%, −15% and −40% (Table 2). Similar results were obtained using the formulations 1-3, 5, 6 and 8.

TABLE 1

Antera 3D Camera results on the examined patients before the treatment and at the end of the treatment.

| Patient number | Overall size of the wrinkle (mm²) | | Average depth of the wrinkle (mm) | | Average width of the wrinkle (mm) | |
|---|---|---|---|---|---|---|
| | Before the treatment | After the treatment | Before the treatment | After the treatment | Before the treatment | After the treatment |
| G1-1 | 129.00 | 104.00 | 0.31 | 0.23 | 1.55 | 1.42 |
| G1-2 | 83.50 | 13.80 | 0.20 | 0.05 | 1.51 | 0.94 |

TABLE 1-continued

Antera 3D Camera results on the examined patients before the treatment and at the end of the treatment.

| Patient number | Overall size of the wrinkle (mm²) | | Average depth of the wrinkle (mm) | | Average width of the wrinkle (mm) | |
|---|---|---|---|---|---|---|
| | Before the treatment | After the treatment | Before the treatment | After the treatment | Before the treatment | After the treatment |
| G1-3 | 11.30 | 11.50 | 0.04 | 0.04 | 1.20 | 1.26 |
| G1-4 | 10.90 | 7.54 | 0.04 | 0.03 | 1.22 | 0.97 |
| G1-5 | 98.60 | 61.50 | 0.23 | 0.16 | 1.55 | 1.34 |
| G1-6 | 58.90 | 21.20 | 0.13 | 0.06 | 1.59 | 1.30 |
| G2-1 | 82.00 | 11.30 | 0.15 | 0.04 | 1.59 | 0.96 |
| G2-2 | 48.40 | 13.70 | 0.11 | 0.06 | 1.50 | 0.63 |
| G2-3 | 10.10 | 3.68 | 0.04 | 0.02 | 1.17 | 1.06 |
| G2-4 | 5.98 | 3.89 | 0.02 | 0.02 | 1.12 | 1.07 |
| G2-5 | 40.10 | 10.10 | 0.10 | 0.04 | 1.39 | 0.98 |
| G2-6 | 19.90 | 5.37 | 0.05 | 0.02 | 1.42 | 0.94 |
| G3-1 | 39.00 | 49.90 | 0.08 | 0.10 | 1.54 | 1.48 |
| G3-2 | 59.60 | 38.40 | 0.12 | 0.09 | 1.59 | 1.38 |
| G3-3 | 11.00 | 9.73 | 0.04 | 0.04 | 1.10 | 1.08 |
| G3-4 | 16.80 | 8.57 | 0.07 | 0.03 | 1.10 | 0.98 |
| G3-5 | 27.50 | 23.20 | 0.07 | 0.06 | 1.37 | 1.18 |
| G3-6 | 27.70 | 18.90 | 0.07 | 0.05 | 1.50 | 1.28 |
| G4-1 | 42.00 | 46.10 | 0.12 | 0.15 | 1.34 | 1.22 |
| G4-2 | 42.60 | 30.30 | 0.09 | 0.07 | 1.51 | 1.24 |
| G4-3 | 11.40 | 10.90 | 0.04 | 0.04 | 1.19 | 1.10 |
| G4-4 | 11.30 | 7.15 | 0.04 | 0.03 | 1.23 | 1.05 |
| G4-5 | 21.30 | 20.40 | 0.06 | 0.07 | 1.33 | 1.18 |
| G4-6 | 25.90 | 9.43 | 0.07 | 0.04 | 1.42 | 0.99 |
| G5-1 | 64.10 | 5.90 | 0.16 | 0.02 | 1.42 | 0.79 |
| G5-2 | 38.00 | 20.10 | 0.08 | 0.05 | 1.52 | 1.50 |
| G5-3 | 20.00 | 4.10 | 0.08 | 0.02 | 1.22 | 0.91 |
| G5-4 | 6.02 | 4.18 | 0.02 | 0.02 | 1.19 | 1.07 |
| G5-5 | 37.90 | 10.60 | 0.12 | 0.03 | 1.31 | 1.09 |
| G5-6 | 20.70 | 8.45 | 0.06 | 0.03 | 1.45 | 1.24 |
| G6-1 | 90.20 | 13.10 | 0.20 | 0.04 | 1.57 | 1.13 |
| G6-2 | 33.80 | 33.20 | 0.08 | 0.10 | 1.35 | 1.18 |
| G6-3 | 13.50 | 5.53 | 0.05 | 0.02 | 1.13 | 1.15 |
| G6-4 | 11.70 | 3.05 | 0.05 | 0.01 | 1.13 | 0.98 |
| G6-5 | 29.50 | 6.34 | 0.07 | 0.02 | 1.45 | 0.94 |
| G6-6 | 20.30 | 7.03 | 0.05 | 0.03 | 1.46 | 0.86 |
| G7-1 | 32.90 | 21.50 | 0.07 | 0.05 | 1.51 | 1.19 |
| G7-2 | 57.80 | 2.63 | 0.12 | 0.01 | 1.57 | 0.68 |
| G7-3 | 6.39 | 6.95 | 0.03 | 0.03 | 1.19 | 1.10 |
| G7-4 | 16.30 | 7.65 | 0.07 | 0.03 | 1.10 | 1.07 |
| G7-5 | 15.30 | 12.90 | 0.04 | 0.04 | 1.26 | 1.20 |
| G7-6 | 33.10 | 2.54 | 0.08 | 0.01 | 1.55 | 0.69 |
| G8-1 | 45.50 | 36.00 | 0.10 | 0.08 | 1.55 | 1.41 |
| G8-2 | 72.10 | 19.60 | 0.17 | 0.05 | 1.56 | 0.84 |
| G8-3 | 9.05 | 7.82 | 0.03 | 0.03 | 1.14 | 1.07 |
| G8-4 | 15.40 | 6.35 | 0.06 | 0.02 | 1.21 | 1.00 |
| G8-5 | 26.50 | 24.80 | 0.07 | 0.07 | 1.37 | 1.35 |
| G8-6 | 19.50 | 12.30 | 0.05 | 0.04 | 1.38 | 1.15 |
| G9-1 | 33.70 | 7.79 | 0.07 | 0.03 | 1.52 | 1.00 |
| G9-2 | 31.20 | 34.70 | 0.08 | 0.08 | 1.52 | 1.46 |
| G9-3 | 5.94 | 4.19 | 0.02 | 0.02 | 1.11 | 0.95 |
| G9-4 | 9.78 | 7.55 | 0.04 | 0.03 | 1.09 | 1.08 |
| G9-5 | 10.70 | 7.07 | 0.03 | 0.03 | 1.29 | 1.10 |
| G9-6 | 19.60 | 20.80 | 0.06 | 0.05 | 1.31 | 1.32 |
| G10-1 | 25.50 | 14.20 | 0.07 | 0.04 | 1.48 | 1.14 |
| G10-2 | 48.70 | 29.50 | 0.10 | 0.06 | 1.56 | 1.21 |
| G10-3 | 8.78 | 6.26 | 0.04 | 0.02 | 1.12 | 1.06 |
| G10-4 | 9.55 | 5.52 | 0.04 | 0.02 | 1.13 | 1.04 |
| G10-5 | 11.50 | 8.32 | 0.04 | 0.03 | 1.05 | 1.06 |
| G10-6 | 30.30 | 23.80 | 0.07 | 0.05 | 1.55 | 1.52 |
| G11-1 | 34.70 | 30.20 | 0.07 | 0.07 | 1.46 | 1.46 |
| G11-2 | 43.40 | 4.57 | 0.09 | 0.01 | 1.59 | 0.71 |
| G11-3 | 5.62 | 5.38 | 0.03 | 0.03 | 0.99 | 0.99 |
| G11-4 | 6.71 | 4.99 | 0.03 | 0.02 | 1.12 | 1.12 |
| G11-5 | 16.00 | 15.70 | 0.04 | 0.04 | 1.39 | 1.34 |
| G11-6 | 14.10 | 8.84 | 0.05 | 0.03 | 1.10 | 1.00 |
| G12-1 | 41.20 | 26.40 | 0.10 | 0.06 | 1.51 | 1.00 |
| G12-2 | 39.40 | 38.70 | 0.09 | 0.10 | 1.59 | 1.49 |
| G12-3 | 12.40 | 6.43 | 0.05 | 0.03 | 1.14 | 1.00 |
| G12-4 | 11.00 | 12.00 | 0.04 | 0.04 | 1.29 | 1.21 |
| G12-5 | 36.00 | 14.00 | 0.10 | 0.04 | 1.31 | 0.77 |
| G12-6 | 19.60 | 25.00 | 0.06 | 0.07 | 1.29 | 1.34 |
| G13-1 | 35.30 | 43.30 | 0.08 | 0.09 | 1.55 | 1.55 |

TABLE 1-continued

Antera 3D Camera results on the examined patients before the treatment and at the end of the treatment.

| Patient number | Overall size of the wrinkle (mm$^2$) | | Average depth of the wrinkle (mm) | | Average width of the wrinkle (mm) | |
|---|---|---|---|---|---|---|
| | Before the treatment | After the treatment | Before the treatment | After the treatment | Before the treatment | After the treatment |
| G13-2 | 21.60 | 18.90 | 0.05 | 0.05 | 1.47 | 1.19 |
| G13-3 | 6.51 | 3.73 | 0.03 | 0.02 | 1.16 | 1.12 |
| G13-4 | 7.62 | 8.07 | 0.03 | 0.03 | 1.15 | 1.21 |
| G13-5 | 22.30 | 26.50 | 0.05 | 0.07 | 1.48 | 1.54 |
| G13-6 | 15.70 | 2.32 | 0.04 | 0.01 | 1.27 | 0.64 |
| G15-1 | 55.10 | 13.20 | 0.12 | 0.05 | 1.55 | 0.94 |
| G15-2 | 28.20 | 26.00 | 0.07 | 0.06 | 1.35 | 1.34 |
| G15-3 | 11.30 | 8.17 | 0.04 | 0.03 | 1.18 | 1.05 |
| G15-4 | 8.14 | 5.49 | 0.03 | 0.02 | 1.10 | 1.01 |
| G15-5 | 33.20 | 10.90 | 0.09 | 0.04 | 1.38 | 0.96 |
| G15-6 | 12.80 | 9.22 | 0.04 | 0.03 | 1.25 | 1.15 |
| G16-1 | 52.90 | 7.48 | 0.11 | 0.02 | 1.44 | 0.82 |
| G16-2 | 47.40 | 37.20 | 0.11 | 0.09 | 1.43 | 1.20 |
| G16-3 | 10.20 | 5.27 | 0.04 | 0.03 | 1.06 | 0.82 |
| G16-4 | 13.80 | 8.43 | 0.05 | 0.03 | 1.23 | 1.09 |
| G16-5 | 30.70 | 8.62 | 0.08 | 0.02 | 1.44 | 1.02 |
| G16-6 | 25.50 | 12.50 | 0.08 | 0.05 | 1.18 | 0.85 |
| G18-1 | 44.00 | 41.30 | 0.10 | 0.09 | 1.53 | 1.42 |
| G18-2 | 23.30 | 19.90 | 0.06 | 0.07 | 1.42 | 1.11 |
| G18-3 | 7.49 | 5.65 | 0.03 | 0.02 | 1.08 | 1.10 |
| G18-4 | 7.50 | 4.68 | 0.03 | 0.02 | 1.05 | 1.06 |
| G18-5 | 19.10 | 12.70 | 0.05 | 0.04 | 1.38 | 1.23 |
| G18-6 | 13.10 | 7.89 | 0.04 | 0.03 | 1.28 | 1.20 |
| G19-1 | 116.00 | 28.00 | 0.26 | 0.08 | 1.56 | 1.06 |
| G19-2 | 88.50 | 57.90 | 0.18 | 0.13 | 1.60 | 1.47 |
| G19-3 | 14.50 | 9.04 | 0.05 | 0.03 | 1.27 | 1.12 |
| G19-4 | 12.40 | 12.10 | 0.04 | 0.05 | 1.25 | 1.14 |
| G19-5 | 26.60 | 11.30 | 0.06 | 0.04 | 1.40 | 1.13 |
| G19-6 | 29.70 | 24.30 | 0.07 | 0.07 | 1.53 | 1.45 |
| G20-1 | 84.20 | 40.60 | 0.16 | 0.09 | 1.58 | 1.29 |
| G20-2 | 114.00 | 104.00 | 0.28 | 0.25 | 1.47 | 1.40 |
| G20-3 | 14.60 | 6.84 | 0.05 | 0.03 | 1.25 | 0.93 |
| G20-4 | 19.00 | 12.50 | 0.07 | 0.04 | 1.16 | 1.17 |
| G20-5 | 52.30 | 45.90 | 0.13 | 0.12 | 1.53 | 1.49 |
| G20-6 | 89.20 | 79.40 | 0.21 | 0.19 | 1.48 | 1.38 |
| G21-1 | 47.40 | 49.10 | 0.12 | 0.12 | 1.46 | 1.40 |
| G21-2 | 40.40 | 29.90 | 0.09 | 0.08 | 1.52 | 1.48 |
| G21-3 | 9.53 | 8.35 | 0.05 | 0.04 | 1.03 | 0.98 |
| G21-4 | 11.70 | 8.88 | 0.05 | 0.04 | 1.14 | 1.09 |
| G21-5 | 25.90 | 26.80 | 0.07 | 0.07 | 1.45 | 1.34 |
| G21-6 | 25.40 | 20.70 | 0.07 | 0.06 | 1.42 | 1.39 |
| G22-1 | 68.20 | 45.40 | 0.18 | 0.12 | 1.25 | 1.19 |
| G22-2 | 128.00 | 89.50 | 0.28 | 0.20 | 1.55 | 1.57 |
| G22-3 | 25.00 | 16.60 | 0.08 | 0.06 | 1.36 | 1.31 |
| G22-4 | 30.50 | 22.90 | 0.10 | 0.08 | 1.27 | 1.25 |
| G22-5 | 34.90 | 24.70 | 0.08 | 0.06 | 1.44 | 1.35 |
| G22-6 | 45.70 | 32.20 | 0.12 | 0.09 | 1.40 | 1.45 |

TABLE 2

Antera 3D Camera: average results on the examined patients before the treatment and at the end of the treatment.

| | Overall size of the wrinkle (mm$^2$) | | Average depth of the wrinkle (mm) | | Average width of the wrinkle (mm) | |
|---|---|---|---|---|---|---|
| | Before the treatment | After the treatment | Before the treatment | After the treatment | Before the treatment | After the treatment |
| AVERAGE VALUES | 32.52 | 19.50 | 0.08 | 0.05 | 1.35 | 1.15 |
| Decrease of the wrinkles after the treatments | −40.05% | | −34.18% | | −15.12% | |

The invention claimed is:

1. Aqueous formulation for topical use containing
trichloroacetate salts at a concentration ranging between 20 and 40% w/w, wherein the trichloroacetate salts are selected from sodium salt (1:1), ammonium salt (1:1), potassium salt (1:1), magnesium salt (2:1), calcium salt (2:1), zinc salt (2:1) and silver salt (1:1),
one or more hydroxyacids at a concentration ranging between 0.5% and 10% w/w, and
optionally glutamic acid or glutamic acid bioisosteres, phytic acid at a concentration ranging between 0.2 and 4.0% w/w, glycerol at a concentration lower than 15% w/w, oxidants at a concentration lower than 1% w/w and a hydrophilic pharmaceutically acceptable gelling agent in concentration up to 7% w/w.

2. A formulation according to claim 1 in which the trichloroacetate salts are present at a concentration of 32-34% w/w.

3. A formulation according to claim 1 in which the hydroxyacid is selected from tartaric acid, citric acid, glycolic acid, glucuronic acid, alpha-hydroxybutyric acid, alpha-hydroxy-isobutyric acid and lactic acid.

4. A formulation according to claim 1 in which the glutamic acid bioisostere is homocysteic acid.

5. A formulation according to claim 1 in which the oxidant is hydrogen peroxide.

6. A formulation according to claim 1 in which the hydrophilic pharmaceutically acceptable gelling agents are selected among hydroxyethyl cellulose, xanthan gum, sclerotium gum, hydroxypropyl starch phosphate, polyacrylamide and $C_{13}$-$C_{14}$ an laureth-7 305 and polyacrylate crosspolymer-6.

7. A formulation according to claim 1 in which the gelling agent is absent.

8. A formulation according to claim 1 in which the gelling agent is present in concentration up to 0.8%.

9. A formulation according to claim 1 in form of compact gel in which the gelling agent is present in concentration up to 7%.

10. Method of treating acne and folliculitis in subjects in need thereof with an antiseptic agent comprising an effective amount of the formulation of claim 1, said method comprising topically applying said formulation and treating said acne and said folliculitis in said subjects.

11. A method of treating skins defects, for cosmetic peels, for stimulation of fibroblast proliferation in subjects in need thereof with an effective amount of the formulation of claim 1, said method comprising
topically applying said formulation to said subjects.

12. The method according to claim 11 wherein said skins defects are rhytides, actinic photodamage, hyperpigmentation and scars.

* * * * *